United States Patent [19]

Martan

[11] 4,069,255
[45] Jan. 17, 1978

[54] PREPARATION OF ACRYLAMIDE
[75] Inventor: Michael Martan, Evanston, Ill.
[73] Assignee: UOP Inc., Des Plaines, Ill.
[21] Appl. No.: 728,353
[22] Filed: Sept. 30, 1976
[51] Int. Cl.$^2$ .......................................... C07C 103/133
[52] U.S. Cl. ............................ 260/561 N; 260/561 R; 252/431 N; 252/474; 75/.5 B; 75/72
[58] Field of Search .................... 260/561 N; 252/474, 252/431 N

[56] References Cited

U.S. PATENT DOCUMENTS

| | | | |
|---|---|---|---|
| 3,966,810 | 6/1976 | Kurata et al. | 260/561 N |
| 3,980,662 | 9/1976 | Watanabe et al. | 260/561 N |
| 3,997,579 | 12/1976 | Jesson et al. | 260/439 R |
| 3,997,606 | 12/1976 | Kane | 260/561 N |

OTHER PUBLICATIONS

Klabunde, Accounts of Chemical Research 8, (1975), pp. 393-399.

*Primary Examiner*—Arthur P. Demers
*Attorney, Agent, or Firm*—James R. Hoatson, Jr.; Raymond H. Nelson; William H. Page, II

[57] ABSTRACT

Acrylamide may be prepared by the hydrolysis of acrylonitrile by treating the acrylonitrile with water in the presence of a copper catalyst which has been prepared by volatilizing copper metal at a temperature in the range of from about 1000° to about 1500° C. in vacuo and condensing the vapors in the presence of an organic solvent.

11 Claims, No Drawings

PREPARATION OF ACRYLAMIDE

BACKGROUND OF THE INVENTION

Acrylamide, in the past few years, has been used increasingly in flocculents and paper strengthening agents. In particular, acrylamide flocculents are becoming more important in the prevention of pollution. Heretofore, a common industrial method of synthesizing acrylamide has been to hydrolyze acrylonitrile in the presence of concentrated sulfuric acid. This process yields acrylamide sulfate which, by the addition of ammonia, is neutralized to form the desired product, acrylamide, plus ammonium sulfate. However, after obtaining the desired product and separating it from the ammonium sulfate, the problem of disposing of the ammonium sulfate is still present. Inasmuch as the value of ammonium sulfate is relatively low and the problem of disposal of the same remains, the conventional means of obtaining acrylamide has now become economically unfeasible to operate. Another problem which is attendant to the production of acrylamide according to the aforementioned method is the difficulty in separating the two compounds in order to obtain a high purity acrylamide product. The separation of the two compounds which involves neutralization before the separation of the acrylamide from ammonium sulfate utilizes a temperature differential in solubilities of the two products. For example, the ammonium sulfate may be removed by filtration and thereafter upon cooling the filtrate the acrylamide is crystallized, separated and dried. Another drawback to this process which has not been heretofore mentioned is that in the hydrolysis step whereby water, concentrated sulfuric acid and acrylonitrile are mixed there must also be polymerization inhibitors present inasmuch as acrylonitrile and acrylamide readily undergo polymerization. Therefore, in order to obtain the desired high purity acrylamide crystals the polymerization inhibitors such as copper, iron salts or sulfur must also be removed and therefore the crystallization rate of the desired acrylamide is reduced.

In addition to the conventional method of synthesizing acrylamide by the hydrolysis of acrylonitrile, it is also known to effect the hydrolysis in the presence of various other catalysts. For example, U.S. Pat. No. 3,579,481 discloses a heterogeneous catalyst which consists essentially of a mixture of silver oxide, zinc oxide or cadmium oxide with chromium oxide. U.S. Pat. No. 3,631,104 discloses a process for converting nitriles to the corresponding amides in which the copper containing catalyst which is utilized has been prepared by reducing copper oxide or a mixture of copper and chromium oxide and copper-molybdenum oxide. In like manner, U.S. Pat. No. 3,767,706 also relates to the hydration of aliphatic nitriles to form amides utilizing a catalytic amount of a catalyst consisting essentially of copper metal. However, the copper metal which is used as the catalyst is prepared by the decomposition and/or reduction of other copper compounds such as copper hydroxide, copper carbonate, copper acetate, copper oxalate, etc. Another U.S. Patent, namely U.S. Pat. No. 3,846,495, discloses a process for catalytically hydrolyzing acrylonitrile to acrylamide by using a copper oxide as a catalyst, said copper oxide having been prepared by contacting an aqueous slurry of copper oxide and powdered alumina with a dilute aqueous solution of an alkali metal hydroxide to yield a slurry which contains copper oxide and powdered aluminum to form the activated catalyst. U.S. Pat. No. 3,928,440 discloses a process for hydrolyzing acrylonitrile with water in the presence of a copper catalyst, said catalyst comprising a particulate copper catalyst which was prepared by contacting alloy particles of copper and aluminum with water at a certain pH for a time sufficient to produce evolution of hydrogen gas from the particles. In addition to the above enumerated patents, U.S. Pat. No. 3,936,502 also discloses a process for producing acrylamide by the hydration of acrylonitrile, said process being effected in the presence of a solid heterogeneous catalyst selected from the group consisting of copper acetylide and copper nitride.

Other catalysts which have been used for the catalytic hydration of acrylonitrile to form acrylamide include manganese oxide or copper oxide in conjunction with acid ion exchange resins.

In contradistinction to the prior art catalysts, it will hereinafter be shown in greater detail that acrylonitrile may be treated with water in the presence of copper catalysts which have been prepared in a manner hereinafter set forth in greater detail whereby improved yields of the desired acrylamide may be obtained.

This invention relates to a method for the preparation of acrylamide. More specifically the invention is concerned with a process for preparing acrylamide whereby acrylonitrile is hydrolyzed in the presence of copper-containing catalysts which have been prepared in a certain manner.

As hereinbefore set forth the use of acrylamide in flocculents, paper strengthening agents and most recently as an additive for tertiary oil recovery has grown in the past. For example, polyacrylamide flocculents cause a more rapid agglomeration and sedimentation than do conventional inorganic flocculents such as ferrous sulfate or aluminum sulfate. Consequently, since pollution with industrial waste water has grown the demand for thick polyacrylamide flocculents has also grown. In addition to its use as a flocculent, polyacrylamide also diplays a higher improving effect on the dry strength of paper than do other paper strengthening agents such as starch or urea-formaldehyde resins. Therefore in view of the increasing use of acrylamide in the above-mentioned fields, it has become more important to develop a method whereby improved yields of the desired product may be obtained without having to have the attendant worry of disposal of unwanted side products or unnecessary separation steps.

It is therefore an object of this invention to provide an improved process for the preparation of acrylamide.

A further object of this invention is to provide an improved process for the production of acrylamide using copper catalysts which have been prepared in a certain manner.

In one aspect an embodiment of this invention resides in a process for the preparation of acrylamide which comprises treating acrylonitrile with water in the presence of a copper catalyst which has been prepared by volatilizing copper metal, subsequently cooling the copper vapors in the presence of an organic solvent, and heating to ambient temperature, and recovering the resultant acrylamide.

A specific embodiment of this invention is found in a process for the preparation of acrylamide which comprises treating acrylonitrile with water at a temperature in the range of from about 60° to about 160° C. in the presence of a copper catalyst in which copper metal has been subjected to volatilization at a temperature in the range of from about 1000° to about 1500° C. in vacuo and subsequently cooled in the presence of tetrahydrofuran, and thereafter recovering the resultant acrylamide.

Other objects and embodiments will be found in the following further detailed description of the present invention.

The desired product is prepared, according to the process of this invention, by treating acrylonitrile with water in the presence of certain catalytic compositions of matter which are prepared in a manner hereinafter set forth in greater detail. By utilizing a copper-containing catalyst which has been prepared according to the process of this invention, the desired product will be obtained in a very high selectivity, the percentage of byproducts such as beta-hydroxypropionyl which results from the hydration of the double bond of the acrylonitrile, being negligible. In addition, the copper will also act as an excellent inhibitor for preventing the polymerization of acrylamide and in addition will not suffer from a fast rate of poisoning which is usually caused by the polymerization of acrylamide which occurs during the reaction. Another factor which is present in the catalyst prepared according to the process of this invention is the relatively high activity. This high activity will be illustrated in the examples which are appended at the end of the specification and is in contrast to other copper-containing catalysts prepared in various other ways. For example, as will be hereinafter shown in greater detail, copper which has been prepared by reduction of CuO powder with molecular hydrogen showed the usual activity. Copper oxide needles or powder which are reduced with molecular hydrogen and thereafter used as a fixed bed catalyst or in a stirred tank reactor will likewise show a very low activity. In contradistinction to this, a catalyst which is prepared by vaporizing copper in an apparatus such as that which is shown in an article in *Accounts of Chemical Research*, 8, 1975 by K. J. Klabunde followed by condensation of the vapor on walls which have been cooled with liquid nitrogen and on which a solvent of the type hereinafter set forth in greater detail is also condensed will form a complex between the metal atoms and the solvent which is stable as a solution at low temperatures. Upon heating the solution to the room or ambient temperature, the complex is decomposed and the resulting copper is present as a very finely dispersed metal powder, the size of the particles of the metal powder being dependent namely upon the nature of the solvent which is employed in the separation of the catalyst.

In the preferred embodiment of the invention the solvents which are employed will comprise polar solvents such as ethers, amines, alcohols, etc. Some specific examples of solvents which may be employed to form the catalyst of the present invention will include alkyl, aryl and heterocyclic ethers such as dimethyl ether, diethyl ether, dipropyl ether, diphenyl ether, dibenzyl ether, di-p-tolyl ether, tetrahydrofuran, tetrahydropyran, dioxane, etc.; alkyl and aromatic amines such as trimethyl amine, triethyl amine, tripropyl amine, tributyl amine, aniline, substituted anilines such as isomeric dimethyl anilines, diethyl anilines, dipropyl anilines, pyridine, alkyl pyridines, nitriles such as acrylonitrile, propionitrile, butyronitrile, etc.; alcohols both alkyl and aryl such as methyl alcohol, ethyl alcohol, n-propyl alcohol, isopropyl alcohol, butyl alcohol, benzyl alcohol, etc. It is to be understood that the aforementioned polar solvents are only representative of the class of compounds which may be employed, and that the present invention is not necessarily limited thereto.

The process of this invention, in which the catalyst which is used is prepared according to the method set forth in the aforementioned article in *Accounts of Chemical Research*, that is, by vaporizing copper metal, thereafter cooling and condensing the copper vapors in a solvent, may be effected by treating the acrylonitrile with water in the presence of said catalyst in an appropriate apparatus such as a Fischer-Porter apparatus. The acrylonitrile is hydrolyzed at temperatures ranging from about 60° to about 160° C. for a period of time which may range from about 0.5 up to about 10 hours or more in duration. While in the preferred embodiment of the invention, the reaction is effected at a pressure of about 60 pounds per square inch, it is also contemplated within the scope of this invention that superatmospheric pressures ranging up to about 100 atmospheres may be employed, the superatmospheric pressure being afforded by the introduction of a substantially inert gas such as nitrogen into the reaction zone. Upon completion of the reaction period the liquid reaction product is separated from the catalyst by decantation or filtration. If there are two phases or layers, the organic layer is separated from the aqueous layer and recycled to the reactor. The aqueous layer which contains unreacted acrylonitrile and acrylamide is subjected to distillation for removal of unreacted acrylonitrile while the remaining aqueous acrylamide solution can be used as such or concentrated to the desired level by evaporation of the water. In the event that crystalline acrylamide constitutes the desired product, it may be obtained by complete evaporation of all of the water which is present.

It is also contemplated within the scope of this invention that the desired acrylamide may be prepared in a continuous manner of operation. When such a type of operation is employed, the starting material comprising the acrylonitrile is continuously charged to a reaction vessel which is maintained at the proper operating conditions of temperature and pressure and which will contain a catalyst which has been prepared by vaporizing copper metal and thereafter cooling the vaporized copper in the presence of a polar solvent of the type hereinbefore set forth in greater detail. The water will also be continuously charged to the reaction zone through a separate line or, if so desired, it may be admixed with the acrylonitrile prior to entry into said reactor and the resulting mixture charged thereto in a single stream. Upon completion of the residence time, the reactor effluent is continuously withdrawn through a filter and the aqueous layer is separated from the organic layer. The organic layer, if one is present, is separated and recycled. Unreacted acrylonitrile is stripped off from the water layer which is concentrated to a point where it contains from 30 to 50% acrylamide, which is a salable material. Because of the high selectivity of the reaction, (i.e., 100%) no purification step is required.

The following examples are given for purposes of illustrating the process of this invention as well as comparing the prior art catalysts with the catalyst herein described. It is to be understood that these examples are given merely for purposes of illustration and that the present invention is not necessarily limited thereto.

EXAMPLE I

To illustrate the hydrolysis of acrylonitrile to acrylamide using a catalyst of the type set forth in the prior art, such a catalyst was prepared by reducing 0.3 grams of copper oxide powder with molecular hydrogen at a temperature in the range of from 150° to 200° C. in a Fischer-Porter pressure apparatus. Upon completion of the reduction, 7.2 grams of acrylamide and 21 grams of water were added to the resulting red copper powder under a nitrogen atmosphere. The reaction was effected at a temperature of 120° C. for a period of 6 hours, at the end of which time there was no detectable amount of acrylamide formed.

The procedure set forth in the above paragraph was repeated with the exception that 4 grams of a reduced copper oxide powder was used as a catalyst in place of the 0.3 grams. After 6 hours of reaction time at a temperature of 120° C., a gas-liquid chromatographic analysis disclosed that 20% of the acrylonitrile was converted, the conversion product comprising 97% acrylamide and 3% beta-hydroxypropionitrile.

EXAMPLE II

This example illustrates the unexpected activity of a catalyst which was prepared by vaporizing copper on a liquid nitrogen temperature controlled wall in which tetrahydrofuran was also condensed. The resulting solution comprised a metal-solvent complex which was stable at low temperatures. After heating the complex to room temperature, a black precipitate formed and the tetrahydrofuran was removed in vacuum. Thereafter 0.1 gram of the vaporized copper catalyst was placed in a nitrogen atmosphere in a Fischer-Porter apparatus provided with a magnetic stirrer, along with 21 cc of water and 9 cc (7.2 grams) of acrylonitrile. The solution was heated to a temperature of 120° C. and maintained thereat for a period of 6 hours, during which time the pressure in the reactor reached 70 psi (pounds per square inch). At the end of the 6-hour period of time, the solution which was recovered was clear and in one phase, the finely divided copper which resulted from the decomposition of the complex settling to the bottom of the solution. The solution was then subjected to gas chromatographic analysis which disclosed that there had been a 40% conversion of the acrylonitrile to acrylamide with no beta-hydroxypropionitrile being detected by the analysis.

It should be noted from a comparison of the above examples that by utilizing a copper-containing catalyst which was vaporized and condensed with a solvent to form a complex, the decomposition of said complex resulting in the obtention of finely divided copper particles, resulted in a conversion of acrylonitrile to acrylamide which was substantially greater than that which was obtained when using a conventional or prior art copper catalyst. In addition, the amount of catalyst which was used in this example was considerably less than the amount of catalyst which was used in the preceding example.

EXAMPLE III

The experiment set forth in Example II was repeated utilizing 0.2 grams of the vaporized copper catalyst which has been prepared in a manner similar to that set forth in the above examples. After heating the acrylonitrile in the presence of 0.2 grams of the catalyst for a period of 6 hours at 120° C., the reaction mixture was centrifuged. The single phase reaction product was subjected to gas-liquid chromatographic analysis, said analysis showing that there had been an 80% conversion of the acrylonitrile to acrylamide with no detactable amount of beta-hydroxypropionitrile being formed as a by-product.

When the experiment was repeated using 0.26 grams of vaporized copper catalyst along with 21 cc of water and 9 cc of acrylonitrile at identical operating conditions, a gas-liquid chromatographic analysis of the reaction product showed that there had been a complete conversion of acrylonitrile to acrymalide.

EXAMPLE IV

In this example a copper catalyst was prepared by vaporizing copper metal in a manner similar to that set forth in Example II above, the exception being that acrylonitrile was used as a solvent in place of the tetrahydrofuran. After recovering the metal-solvent complex, it was heated to room temperature, a slurry being formed which contained 0.25 grams of copper and 25 grams of acrylonitrile. This slurry along with 75 grams of water were placed in a Fischer-Porter apparatus similar to that described in Example I above. The reaction was effected in a nitrogen atmosphere for a period of 6 hours at 120° C. At the end of this time, a gas-liquid chromatographic analysis disclosed that 36% of the acrylonitrile had been converted to acrylamide.

EXAMPLE V

To illustrate the continued activity of a catalyst which has been prepared according to the method hereinbefore set forth, the catalyst which was utilized in Example II was isolated and reused in an experiment similar to that set forth in Example II above. After a reaction time of 6 hours at 120° C. using 9 cc of acrylonitrile and 21 cc of water, the reaction product was subjected to gas-liquid chromatographic analysis which disclosed that 36% of the acrylonitrile had been converted to acrylamide. This illustrates that the catalyst retained its activity and therefore may be reused for a number of cycles to convert acrylonitrile to acrylamide.

I claim as my invention:

1. A process for the preparation of acrylamide which comprises treating acrylonitrile with water at hydrolysis conditions in the presence of a catalyst comprising finely divided metallic copper and prepared by volatilizing copper metal, subsequently cooling the copper vapors in contact with an organic solvent and heating to ambient temperature, and recovering the resultant acrylamide.

2. The process as set forth in claim 1 in which said hydrolysis conditions include a temperature in the range of from about 60° to about 160° C.

3. The process as set forth in claim 1 in which said copper is volatilized at a temperature in the range of from about 1000° to about 1500° C. in vacuo.

4. The process as set forth in claim 1 in which said organic solvent is an ether.

5. The process as set forth in claim 4 in which said ether is tetrahydrofuran.

6. The process as set forth in claim 4 in which said ether is tetrahydropyran.

7. The process as set forth in claim 1 in which said solvent is acrylonitrile.

8. The process as set forth in claim 4 in which said ether is dioxane.

9. The process as set forth in claim 1 in which said copper catalyst is absorbed on a solid support.

10. The process as set forth in claim 9 in which said support is alumina.

11. The process as set forth in claim 9 in which said support is silica.

* * * * *